United States Patent
Li

(10) Patent No.: US 10,321,872 B2
(45) Date of Patent: *Jun. 18, 2019

(54) MULTI-PURPOSE WEARABLE PATCH FOR MEASUREMENT AND TREATMENT

(71) Applicant: VivaLnk, Inc., Santa Clara, CA (US)

(72) Inventor: Jiang Li, Cupertino, CA (US)

(73) Assignee: VivaLnk, Inc., Campbell, CA (US)

(*) Notice: Subject to any disclaimer, the term of this patent is extended or adjusted under 35 U.S.C. 154(b) by 266 days.

This patent is subject to a terminal disclaimer.

(21) Appl. No.: 15/472,641

(22) Filed: Mar. 29, 2017

(65) Prior Publication Data

US 2018/0256100 A1 Sep. 13, 2018

Related U.S. Application Data

(63) Continuation-in-part of application No. 15/457,532, filed on Mar. 13, 2017, now Pat. No. 10,111,618.

(51) Int. Cl.
| | |
|---|---|
| *A61N 1/00* | (2006.01) |
| *A61B 5/00* | (2006.01) |
| *A61B 5/01* | (2006.01) |
| *A61B 5/021* | (2006.01) |
| *A61F 7/00* | (2006.01) |
| *A61N 1/04* | (2006.01) |
| *A61N 1/36* | (2006.01) |

(52) U.S. Cl.
CPC ............ *A61B 5/4836* (2013.01); *A61B 5/01* (2013.01); *A61B 5/021* (2013.01); *A61B 5/6816* (2013.01); *A61B 5/6833* (2013.01); *A61F 7/007* (2013.01); *A61N 1/0492* (2013.01); *A61N 1/36031* (2017.08); *A61F 2007/0005* (2013.01); *A61F 2007/0071* (2013.01); *A61F 2007/0078* (2013.01); *A61F 2007/0096* (2013.01); *A61N 1/36025* (2013.01)

(58) Field of Classification Search
CPC ....... A61B 5/4836; A61B 5/6833; A61B 5/01; A61B 5/6816; A61B 5/021; A61N 1/36031; A61N 1/0492; A61N 1/36025; A61N 1/36014; A61F 7/007; A61F 2007/0071; A61F 2007/0005; A61F 2007/0096; A61F 2007/0078
See application file for complete search history.

(56) References Cited

U.S. PATENT DOCUMENTS

| | | | | |
|---|---|---|---|---|
| 5,423,874 | A * | 6/1995 | D'Alerta | ............ A61N 1/36021 607/46 |
| 9,277,864 | B2 * | 3/2016 | Yang | ........................ A61B 5/00 |

(Continued)

*Primary Examiner* — Mallika D Fairchild
(74) *Attorney, Agent, or Firm* — SV Patent Service

(57) ABSTRACT

A multi-purpose wearable patch includes a stretchable and permeable substrate, a first sensing unit mounted in the stretchable and permeable substrate, the sensing unit that can conduct a first measurement of a user to produce a first measurement signal, a treatment unit that produces a first treatment field in the user's body; a circuit electrically connected with the treatment unit and the sensing unit; and a semiconductor chip in connection with the circuit and configured to receive the first measurement signal from the sensing unit. The semiconductor chip produces a first treatment control signal to control the treatment unit to produce a first treatment field in the user's body.

17 Claims, 4 Drawing Sheets

(56) References Cited

U.S. PATENT DOCUMENTS

| | | | |
|---|---|---|---|
| 2002/0107436 A1* | 8/2002 | Barton | A61B 5/0008 600/382 |
| 2003/0014091 A1* | 1/2003 | Rastegar | A61N 1/08 607/61 |
| 2007/0270672 A1 | 11/2007 | Hayter | |
| 2008/0287747 A1* | 11/2008 | Mestrovic | H05K 1/147 600/300 |
| 2009/0171180 A1 | 7/2009 | Pering | |
| 2011/0137381 A1* | 6/2011 | Lee | A61N 1/0529 607/62 |
| 2012/0242481 A1 | 9/2012 | Gemandt | |
| 2016/0015962 A1* | 1/2016 | Shokoueinejad Maragheh | A61N 5/0616 607/50 |
| 2017/0136264 A1* | 5/2017 | Hyde | A61N 7/00 |

* cited by examiner

MULTI-PURPOSE WEARABLE PATCH FOR MEASUREMENT AND TREATMENT

BACKGROUND OF THE INVENTION

The present application relates to wearable electronic devices, and in particular, to wearable patches that can attach to human skin.

Electronic patches can be used for tracking objects and for performing functions such as producing sound, light or vibrations, and so on. As applications and human needs become more sophisticated and complex, electronic patches are required to perform a rapidly increasing number of tasks. Electronic patches are often required to be conformal to curved surfaces, which in the case of human body, can vary overtime.

Electronic patches can communicate with smart phones and other devices using WiFi, Bluetooth, Near Field Communication (NFC), and other wireless technologies. NFC is a wireless communication standard that enables two devices to quickly establish communication within a short range around radio frequency of 13.56 MHz. NFC is more secure than other wireless technologies such as Bluetooth and Wi-Fi because NFC requires two devices in close proximity (e.g. less than 10 cm). NFC can also lower cost comparing to other wireless technologies by allowing one of the two devices to be passive (a passive NFC tag).

Bluetooth is another wireless communication standard for exchanging data over relatively longer distances (in tens of meters). It employs short wavelength UHF radio waves from 2.4 to 2.485 GHz from fixed or mobile devices. Bluetooth devices have evolved to meet the increasing demand for low-power solutions that is required for wearable electronics. Benefited from relatively longer reading distance and active communication, Bluetooth technologies allow wearable patches to continuously monitoring vital information without human interference, which is an advantage over NFC in many applications.

Wearable patch (or tag) is an electronic patch to be worn by a user. A wearable patch is required to stay on user's skin and operate for an extended period of time from hours to months. A wearable patch can contain a micro-electronic system that can be accessed using NFC, Bluetooth, WiFi, or other wireless technologies. A wearable patch can be integrated with different sensors for measurements such as vital signs monitoring.

Traditionally, treatments can be conducted on patients using probes wire connected with heavy immobile equipment. For example, Cranial Electrotherapy Stimulation (CES) utilizes extremely small levels of electrical stimulation across the head of a patient for therapeutic treatment of anxiety, depression, insomnia and chronic pain.

There is therefore a need for convenient measurement of a patient's vital signs and other signals and treatment of the patient's symptoms.

SUMMARY OF THE INVENTION

The presently disclosure discloses a dual-purpose wearable device that can conveniently measure a patient's vital signs and other signals and treat the patient's symptoms. The disclosed wearable patch is easy and comfortable to wear by patients and do not require wire connections to heavy equipment.

Moreover, measurements and treatments can be conducted by the disclosed dual purpose wearable patch and the disclosed multi-purpose wearable patch while a patient fulfills his or her normal daily activities. Thus treatments can be timely and dynamically applied which such needs arise according to measurements of vital body signals and other signals.

Furthermore, effects of treatments can be immediately monitored by the dual purpose wearable patch and the disclosed multi-purpose wearable patch after it applies treatment.

In one general aspect, the present invention relates to a multi-purpose wearable patch that includes a stretchable and permeable substrate, a first sensing unit mounted in the stretchable and permeable substrate, the sensing unit that can conduct a first measurement of a user to produce a first measurement signal, a treatment unit that can produce a first treatment field in the user's body; a circuit electrically connected with the treatment unit and the sensing unit; and a semiconductor chip in connection with the circuit and configured to receive the first measurement signal from the sensing unit, wherein the semiconductor chip can produce a first treatment control signal to control the treatment unit to produce a first treatment field in the user's body Implementations of the system may include one or more of the following. The treatment unit can include a heater, wherein the semiconductor chip can produce the first treatment control signal to control the heater to produce heat in the user's body. The treatment unit can include one or more electrodes, wherein the semiconductor chip is configured to produce the first treatment control signal to control the one or more electrodes to apply a voltage across the user's body. The semiconductor chip can produce a second treatment control signal to control the treatment unit to produce a second treatment field in the user's body. The semiconductor chip can control to control the treatment unit to produce the first treatment field in the user's body in response to the first measurement signal. The semiconductor chip can vary a type, timing, a frequency, or duration of the first treatment field in the user's body based on the first measurement signal. The semiconductor chip can control the first sensing unit to vary a type, timing, a frequency, or duration of the first measurement of the user based on the treatment field applied across the user's body. The semiconductor chip can switch the treatment unit and the sensing unit between a measurement mode and a treatment mode. The first sensing unit can include a mechanical sensor configured to measure a pulse or blood pressure of the user's body. The first sensing unit can include a temperature sensor configured to measure a temperature of the user's skin or body. The multi-purpose wearable patch can further include a second sensing unit to conduct a second measurement of a user to produce a second measurement signal. The semiconductor chip can control to control the treatment unit to produce the first treatment field in the user's body in response to the first measurement signal and the second measurement signal. The semiconductor chip can vary a type, timing, a frequency, or duration of the first treatment field in the user's body based on the first measurement signal and the second measurement signal. The second sensing unit can include a mechanical sensor configured to measure a pulse or blood pressure of the user's body, or a temperature sensor configured to measure a temperature of the user's skin or body. The multi-purpose wearable patch can further include a circuit substrate comprising the circuit and on the stretchable and permeable substrate, wherein the semiconductor chip is mounted on the circuit substrate; and a battery configured to supply power to the circuit and the semiconductor chip. The multi-purpose wearable patch can further include an antenna in electric connection with the semiconductor chip, wherein the semiconductor chip is configured to produce electric signals to enable the antenna to wirelessly exchange measurement data based on the first measurement signal with an external device, wherein the semiconductor chip is configured to produce electric signals to enable the antenna to wirelessly exchange treatment data with an external device, wherein the treatment control signal is at least in part based on the treatment data. The multi-purpose wearable patch can further include an adhesive layer between the stretchable and permeable substrate and the circuit substrate. The multi-purpose wearable patch can further include an elastic layer formed on the stretchable and permeable substrate, the circuit substrate, and the sensing unit.

In another aspect, the present invention relates to a dual purpose wearable patch that includes a stretchable and permeable substrate; a sensing unit mounted in the stretchable and permeable substrate, wherein the sensing unit is configured to conduct a measurement of a user to produce a measurement signal; one or more electrodes respectively attached to the stretchable and permeable substrate; a circuit substrate on the stretchable and permeable substrate, wherein the circuit substrate comprises a circuit electrically connected with the one or more electrodes and the sensing unit; and a semiconductor chip mounted on the circuit substrate and in connection with the circuit, wherein the semiconductor chip is configured to receive the measurement signal from the sensing unit, wherein the semiconductor chip can produce a treatment control signal to control the one or more electrodes to apply a voltage across the user's body.

Implementations of the system may include one or more of the following. The semiconductor chip can produce a treatment control signal to control the one or more electrodes to apply a voltage across the user's body in response to a measurement signal. The dual purpose wearable patch can further include a battery configured to supply power to the circuit and the semiconductor chip. The semiconductor chip can switch the circuit, the one or more electrodes, and the sensing unit into or off from a measurement mode and a treatment mode. The one or more electrodes can include a second electrode and a third electrode configured to apply a voltage across the user's body. The sensing unit can include a temperature sensor configured to measure the user's skin temperature, wherein the measurement signal comprises temperature data. The sensing unit can further include a thermally conductive cup having a bottom portion mounted in a first opening in the stretchable and permeable substrate, wherein the temperature sensor is positioned inside and is in thermal conduction cup with the conductive cup. The sensing unit can include a thermally-conductive adhesive that fixes the temperature sensor to an inner surface of the conductive cup; and a thermally insulating material in a top portion of the conductive cup. The sensing unit can include an accelerometer configured to measure movement of the user. The sensing unit can include a pressure sensor or a force sensor configured to measure blood pressure or pulse of the user. The semiconductor chip can control a type, a frequency, or duration of a measurement of the user by the sensing unit based on the voltage applied across the user's body. The dual purpose wearable patch can further include an antenna mounted on the circuit substrate and in electric connection with the semiconductor chip, wherein the semiconductor chip is configured to produce electric signals to enable the antenna to wirelessly exchange measurement data based on the measurement signal with an external device, wherein the semiconductor chip can produce electric signals to enable the antenna to wirelessly exchange treatment data with an external device, wherein the treatment control signal is at least in part based on the treatment data. At least one of the one or more electrodes can include an electrically conductive cup that is electrically connected to the control circuit in the circuit substrate, wherein the stretchable and permeable substrate comprises a second opening in which the electrically conductive cup is mounted. The electrically conductive cup can be electrically connected with the circuit. The dual purpose wearable patch can further include an adhesive layer between the stretchable and permeable substrate and the circuit substrate. The dual purpose wearable patch can further include an elastic layer formed on the stretchable and permeable substrate, the circuit substrate, and the sensing unit. The sensing unit includes an accelerometer can measure the user's movement, wherein the measurement signal comprises movement data. The sensing unit can include a pressure sensor or a force sensor configured to measure the user's blood pressure and/or the user's pulse, wherein the measurement signal comprises pulse data and blood pressure data.

These and other aspects, their implementations and other features are described in detail in the drawings, the description and the claims.

DETAILED DESCRIPTION OF THE INVENTION

Figure 1:
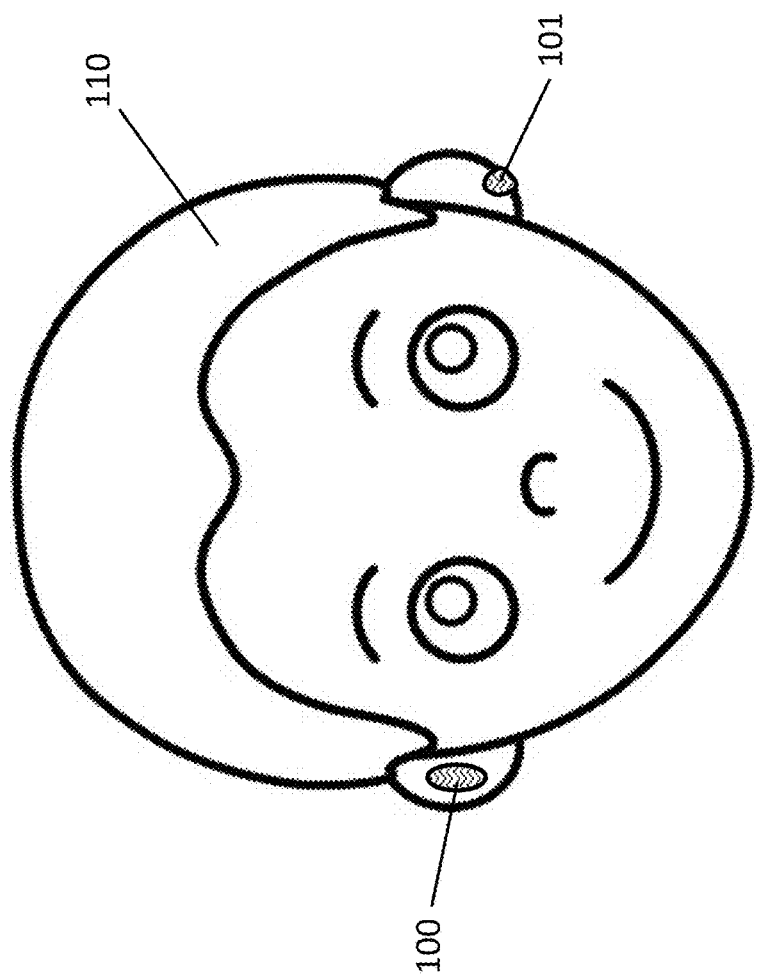
FIG. 1 illustrates multi-purpose wearable patches attached to a user's skin.

Referring to FIG. 1, one or more multi-purpose wearable patches 100, 101 are attached to the skin of a user 110 for measuring body vital signs. The multi-purpose wearable patch 100 can be placed on the ears, the forehead, the hands, the shoulder, the waist, the leg, or the foot, under the armpit, around the wrist, on or around the arm, or other parts of a user's body. In the present disclosure, the term "wearable patch" can also be referred to as "wearable sticker", "wearable tag", or "wearable band", etc. In the present disclosure, "a multi-purpose wearable patch" also includes "a dual purpose wearable patch".

As discussed in more detail below, multi-purpose wearable patches 100, 101 can operate individually, or in a group to provide certain desired treatment or measurement. For example, the multi-purpose wearable patch 101 can wrap around a user's ear for applying an electric field through certain location of the ear. Similar, the disclosed multi-purpose wearable patch can wrap around a user's wrist for providing treatment and measurement. Moreover, the multi-purpose wearable patches 100, 101 can be attached to different parts of a user's body such as on the two ears or the two temples of the user 100, which allows a low electric voltage signal to be applied across the user's head.

In accordance to the present invention, the disclosed multi-purpose wearable patch includes a treatment portion and a measurement portion. The measurement portion can measure vital signs, motion track, skin temperature, and ECG signals. The treatment portion can apply electrical signals, heat, and sometimes force or pressure to user's body.

Figure 2:
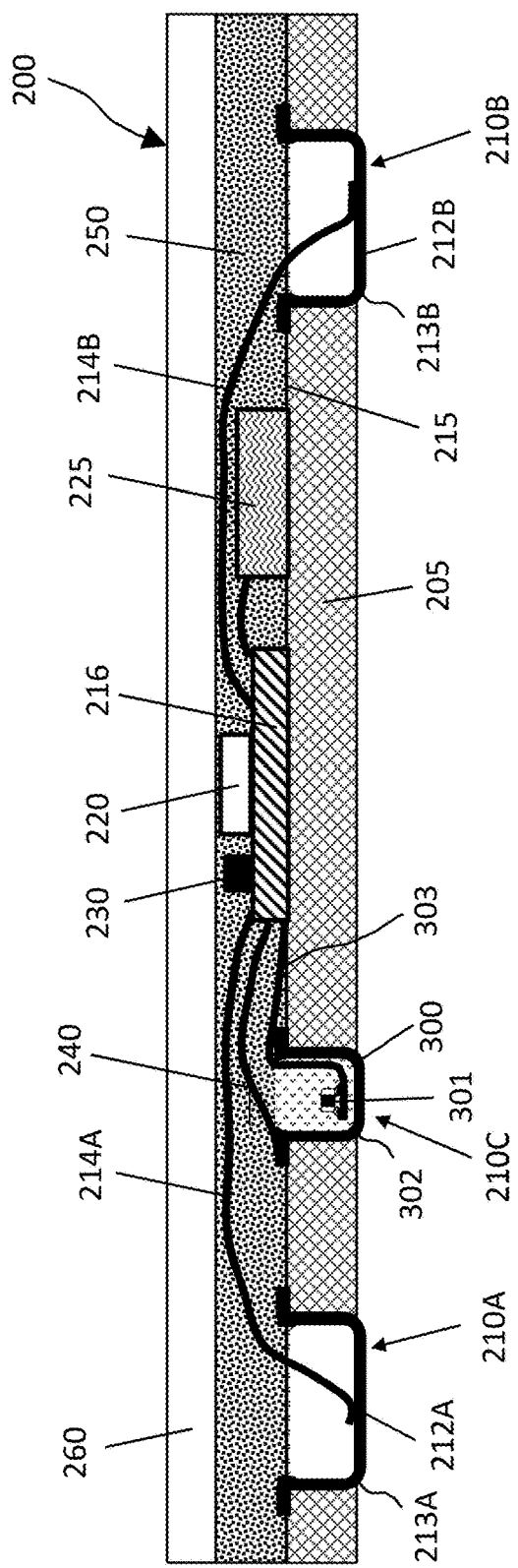
FIG. 2 is a cross-sectional view of an exemplified dual purpose wearable patch for measurement and treatment in accordance with some embodiments of the present invention.
Figure 3:
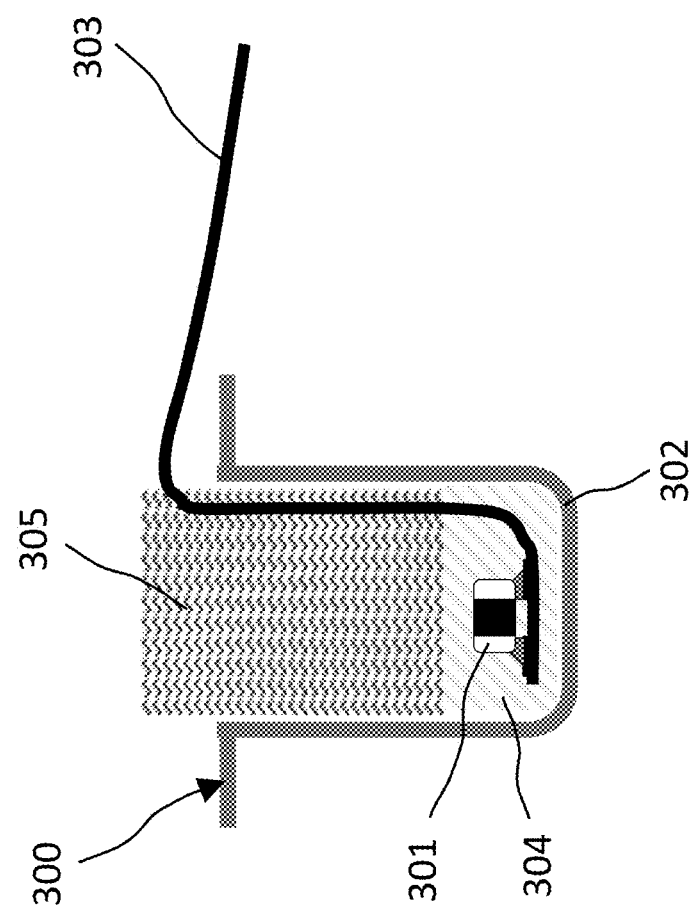
FIG. 3 is a detailed cross-sectional view of an exemplified sensing unit in the dual purpose wearable patch of FIG. 2.

In some embodiments, referring to FIGS. 2 and 3, an exemplified dual purpose wearable patch 200 includes a stretchable and permeable substrate 205 that include openings 210A, 210B, 210C. The stretchable and permeable substrate 205 can be made of soft foam materials such as EVA, PE, CR, PORON, EPD, SCF or fabric textile, to provide stretchability and breathability. The measurement portion of the disclosed dual purpose wearable patch 200 includes a sensing unit 300 mounted in the opening 210C. The treatment portion of the disclosed dual purpose wearable patch 200 includes two electrodes 212A, 212B, respectively comprising electrically conductive cups 213A, 213B, are mounted in the openings 210A, 210B. A circuit substrate 216 and a battery 225 are bonded to the stretchable and permeable substrate 205 by an adhesive layer 215 pre-laminated on the stretchable and permeable substrate 205. A semiconductor chip 220 and an antenna 230 are mounted on the circuit substrate 216. The circuit substrate 216 includes an electric circuit therein and can for example be implemented with a printed circuit board.

The thermal conductive cup 302 in the sensing unit 300 is electrically connected with the circuit substrate 216 by a conductive line 240, which in turn establishes electrical communication between the thermal conductive cup 302 and the semiconductor chip 220.

An elastic layer 250 is also bonded to the stretchable and permeable substrate 205 by the adhesive layer 215 to the stretchable and permeable substrate 205, and is also formed on the circuit substrate 216, the sensing unit 300, and the electrodes 212A, 212B. The elastic layer 250 can be formed by soft stretchable and permeable foam materials such as EVA, PE, CR, PORON, EPD, SCF, or fabric textile. A thin film 260 is formed on the elastic layer 250 for protection and cosmetic purposes.

In usage, an adhesive material formed on the lower surface of the stretchable and permeable substrate 205 is attached the user's skin, so that the bottom of the thermal conductive cup 302 is in tight contact with a user's skin to accurately measure temperature, electrical, or pressure signals from the user's skin, or apply electrical, thermal, or mechanical signals to the user's skin. The semiconductor chip 220 receives an electric signal from the temperature sensor 301 in response to a temperature measurement of the user's skin.

The Treatment Portion

In some embodiments, the electrically conductive cups 213A, 213B in the electrodes 212A, 212B are respectively electrically connected to the electric circuit in the circuit substrate 216 by conductive lines 214A, 214B (e.g. flexible ribbons embedded with conductive circuits). In accordance with the present application, the electrodes 212A, 212B can also be implemented in other configurations such as conductive pins, conductive pads, conductive buttons, or conductive strips. The semiconductor chip 220 can produce treatment electric signals, which can be amplified by an amplifier (not shown in FIG. 2) with power supplied by the battery 225, which is sent to the electrodes 212A, 212B via the conductive lines 214A, 214B.

In some embodiments, the electric voltage (typically in low amplitude) generated across the electrodes 212A, 212B is applied to the user's skin for therapeutic treatment. For example, such Cranial Electrotherapy Stimulation treatment can be applied across the electrode in one disclosed dual purpose wearable patch across a user's ear lobe (e.g. 101 in FIG. 1) or across a user's wrist. In another example, electrical voltage signals can be applied across electrodes in two disclosed dual purpose wearable patches (e.g. 100, 101 in FIG. 1). In this case, a thin conductive wire behind the user's neck can be tethered to the two dual purpose wearable patches to provide proper ground for the voltage signals.

The semiconductor chip 220 can communicate with an external device such as a mobile phone or a computer via the antenna 230 in wireless signals. For example, the semiconductor chip 220 can receive a treatment plan from the external device. The wireless signal can be based on using WiFi, Bluetooth, Near Field Communication (NFC), and other wireless standards. The semiconductor chip 220 can general the treatment electric signals at durations, intervals, and amplitudes as defined in the treatment plan.

When the dual purpose wearable patch 200 is worn by a user, the antenna 230 is separated from the user's skin by the circuit substrate 216 and the stretchable and permeable substrate 205, which minimizes the impact of the user's body on the transmissions of wireless signals by the antenna 230.

Dynamic Treatment

In some embodiments, the semiconductor chip 220 can general the treatment electric signals at durations, intervals, and amplitudes based on the measurement data obtained from the sensing unit 300, as described below. For example, the electrotherapy stimulation treatment can be adjusted based on the user's skin temperature, heart beats, and blood pressure measured by the sensing unit 300. User's bio vital signals may indicate user's stress levels, which can be treated by appropriate waveforms of electrical signals.

The Measurement Portion

In some embodiments, in the measurement portion of the disclosed dual purpose wearable patch 200, the sensing unit 300 includes a temperature sensor 301 in a thermal conductive cup 302 which has its bottom portion mounted into the large opening 210C and fixed to the stretchable and permeable substrate 205 by an adhesive. The temperature sensor 301 is electrically connected to the electric circuit in the circuit substrate 216 by a flexible conductive ribbon 303. Referring to FIG. 3, the bottom portion of the thermal conductive cup 302 protrudes out of the lower surface of the stretchable and permeable substrate 205. The lips of the thermal conductive cup 302 near its top portion are fixedly attached or bonded to bonding pads (not shown) on the stretchable and permeable substrate 205 by soldering or with an adhesive. The thermal conductive cup 302 is both thermally and electrically conductive. The thermal conductive cup 302 can be made of a thermally conductive metallic or alloy material such as copper, stainless steel, ceramic or carbide composite materials.

The temperature sensor 301 is attached to an inner surface near the bottom of the thermal conductive cup 302. The temperature sensor 301 can be implemented, for example, by a thermistor, a Resistor Temperature Detector, or a Thermocouple. The temperature sensor 301 is in thermal conduction with the thermal conductive cup 302. When an outer surface of the bottom portion of the thermal conductive cup 302 is in contact with a user's skin, the thermal conductive cup 302 thus effectively transfers heat from a user's skin to the temperature sensor 301. A flexible conductive ribbon 303 is connected to the temperature sensor 301 in the thermal conductive cup 302 and to the electric circuit in the stretchable and permeable substrate 205.

The temperature sensor 301 can send an electric signal to the semiconductor chip 220 via the electric circuit in response to a measured temperature. The semiconductor chip 220 processes the electric signal and output another electrical signal which enables the antenna 230 to transmit a wireless signal carrying the measurement data to another external device such as a mobile phone or a computer (its wireless signals, as described below, can be boosted by a charging and wireless boosting station). The wireless signal can be based on using WiFi, Bluetooth, Near Field Communication (NFC), and other wireless standards. The battery 225 powers the semiconductor chip 220, the antenna 230, the first and the second electric circuits, and possibly the temperature sensor 301.

The temperature sensor 301 can be fixed to an inner surface at the bottom of the thermal conductive cup 302 by a thermally-conductive adhesive 304, which allows effective heat transfer from the bottom of the thermal conductive cup 302 to the temperature sensor 301. Examples of the thermally-conductive adhesive 304 can include electrically-insulative thermally-conductive epoxies and polymers. A thermally insulating material 305 filling the top portion of the thermal conductive cup 302 fixes the thermally-conductive adhesive 304 at the bottom of the thermal conductive cup 302 and reduces heat loss from the temperature sensor 301 to the elastic layer (described below) or the environment. The flexible conductive ribbon 303 can be bent and laid out along the wall the thermal conductive cup 302.

Further details of the sensing unit are disclosed in the commonly assigned co-pending U.S. patent application Ser. No. 15/224,121 "Wearable thermometer patch for accurate measurement of human skin temperature", filed Jul. 29, 2016, the disclosure of which is incorporated herein by reference.

In some embodiments, the sensing unit 300 includes an accelerometer that can measure acceleration and movement of the user. In some embodiments, the sensing unit 300 includes a pressure sensor or a force sensor that can measure the user's pulses or blood pressure during or outside treatments.

In some embodiments, the sensing unit 300 includes one or more electrodes for measuring ECG signals. The electrode can for example be structured in an electrically conductive cup similar to the thermal conductive cup 302 described above. The ECG signal (voltage) can be measured across two of the electrodes or across one of the electrodes and one of the electrodes 212A, 212B (used as ground). In particular, the ECG signals can be measured when the electrotherapy simulation treatment is not conducted.

In some embodiments, the sensing unit 300 can include multiple sensors for temperature, movement, blood pressure, moisture, and pulse measurements.

Dynamic Measurement

In some embodiments, the semiconductor chip 220 can control the type(s), the timing, and frequencies of the measurement(s) by the sensing unit 300 in response to the types of treatment applied. For example, based on the timing, the durations, intervals, and amplitudes of the treatment electric signals, the frequencies, the durations and the type(s) of the measurement(s) can be varied to more accurately and more timely monitor the user's health conditions.

Mode Switching

The semiconductor chip 220 can control the circuit to switch the sensing unit 300 and the electrodes 210A, 210B into or off from a measurement mode, or into or off from a treatment mode. The mode switching can be specified in the treatment plan received from an external device, or dynamically adjusted according to the user's vital signals and responsiveness to treatment.

Personalized Medicine

Since the disclosed dual purpose wearable patch is worn by an individual patient, the disclosed dual purpose patch is ideal for personalized medical treatment. Each treatment plan download into the disclosed dual purpose wearable patch can be individualized according to the patient's needs.

Moreover, the disclosed dual purpose wearable patch can significantly enhance the effectiveness of individualized treatments for patients. In particular, treatments can be dynamically adjusted according to the current condition of the user as indicated by the bio vital signals currently measured from the user.

Multi-Purpose Wearable Patch

Figure 4:
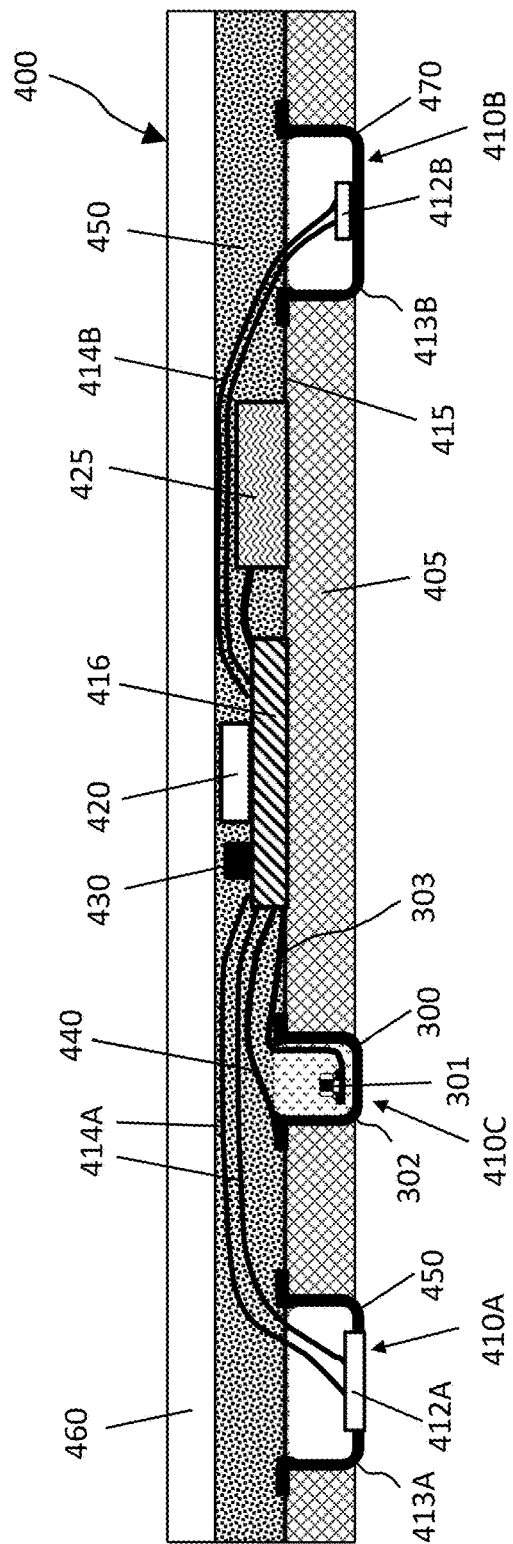
FIG. 4 is a cross-sectional view of an exemplified multi-purpose wearable patch for measurement and treatment in accordance with some embodiments of the present invention.

In some embodiments, referring to FIG. 4, a multi-purpose wearable patch 400 includes a stretchable and permeable substrate 405 that includes openings 410A, 410B, 410C. The stretchable and permeable substrate 405 can be made of soft foam materials such as EVA, PE, CR, PORON, EPD, SCF or fabric textile, to provide stretchability and breathability. A circuit substrate 416 and a battery 425 are bonded to the stretchable and permeable substrate 405 by an adhesive layer 415 pre-laminated on the stretchable and permeable substrate 405. A semiconductor chip 420 and an antenna 430 are mounted on the circuit substrate 416. The circuit substrate 416 includes an electric circuit therein and can for example be implemented with a printed circuit board.

In the multi-purpose wearable patch 400, the semiconductor chip 420 receives and processes different types of measurement signals from different sensing units. The measurement signals can reflect the user's health, mental, and psychological states. The semiconductor chip 420 can send out treatment signals for controlling treatment portion to conduct treatments on the user (e.g. thermal, electrical, mechanical, etc.).

The multi-purpose wearable patch 400 includes a measurement portion that includes a sensor unit 450 mounted in the opening 410A and a sensing unit 300 mounted in the opening 410C. The sensing unit 300 includes a temperature sensor 301 in a thermal conductive cup 302 which has its bottom portion mounted into the large opening 410C and fixed to the stretchable and permeable substrate 405 by an adhesive. The temperature sensor 301 is electrically connected to the electric circuit in the circuit substrate 416 by a flexible conductive ribbon 303. When an outer surface of the bottom portion of the thermal conductive cup 302 is in contact with a user's skin, the thermal conductive cup 302 thus effectively transfers heat from a user's skin to the temperature sensor 301. A flexible conductive ribbon (303 in FIG. 3) is connected to the temperature sensor 301 in the thermal conductive cup 302 and to the electric circuit in the stretchable and permeable substrate 405. The temperature sensor 301 can send an electric signal to the semiconductor chip 420 via the electric circuit in response to a measured temperature. Details about the sensing unit 300 are described above in relation to FIG. 3.

The thermal conductive cup 302 in the sensing unit 300 can be electrically conductive. The thermal conductive cup 302 is electrically connected with the circuit substrate 416 by a conductive line 440, which establishes electrical communication between the thermal conductive cup 302 and the semiconductor chip 420. When the thermally and electrically conductive cup 302 is in electric contact with a user's skin, the semiconductor chip 420 can receive an EEG signal via the conductive cup 302 from the skin of the user.

The sensor unit 450 includes a cup 413A and a mechanical sensor 412A mounted in a window at the bottom of the cup 413A. The mechanical sensor 412A can detect a pressure or a vibration in the user skin or body when the bottom of the cup 413A is in contact of the user's skin. The mechanical sensor 412A can include a piezoelectric material that produce electrical signal in response to pressure or stress. In one implementation, the mechanical sensor 412A can include a membrane coated with a piezoelectric material that produces an electrical signal in response to pressure, mechanical disturbances, or vibrations. In some implementations, the mechanical sensor 412A is an integrated micromechanical electrical system (MEMS) device that can be micro-fabricated on a semiconductor substrate. When the mechanical sensor 412A is in contact with user's skin, the vibrations or pressure variations caused by the user's heart beats and blood pressure can be detected; the mechanical sensor 412A sends a measurement signal to the semiconductor chip 420 via conductive lines 414A. The semiconductor chip 420 can extract the user's pulse and blood pressure information from the measurement signal.

Other measurements compatible with the multi-purpose wearable patch can include movement, acceleration, moisture, etc.

The disclosed multi-purpose wearable patch 400 includes a treatment unit 470 that includes a heater 412B attached to a thermally conductive cup 413B mounted in the opening 410B. The heater 412B can be a thermal resistor that produces heat when applied with a voltage. The heater 412B is electrically connected to the electric circuit in the circuit substrate 416 via conductive lines 414B can be controlled by the semiconductor chip 420. The semiconductor chip 420 can produce treatment electric signals, which can be amplified by an amplifier (not shown in FIG. 4) with power supplied by the battery 425, which is sent to control the heater 412B via the conductive lines 414B. Under the control the treatment electric signals, the heater 412B can produce heat to treat the user's skin and body. The heating can be applied in different waveforms such as static, pulses, and waveforms of varying frequencies. Heat treatments can be used to reduce or cure muscle or joint pains, mental stress, and to increase blood circulation, etc. As described above, the treatment unit 470 can also include electrodes that produce electrical voltage across the user's skin or body under the control of the semiconductor chip 420. In general, the treatment unit 470 can produce treatment field(s) in the user the skin or body, such treatments including electrical, heat, mechanical, magnetic and other fields, which can provide therapy or relaxation to the user.

An elastic layer 450 is also bonded to the stretchable and permeable substrate 405 by the adhesive layer 415 to the stretchable and permeable substrate 405, and is also formed on the circuit substrate 416, the sensing unit 300, the mechanical sensor 412A, and the heater 412B. The elastic layer 450 can be formed by soft stretchable and permeable foam materials such as EVA, PE, CR, PORON, EPD, SCF, or fabric textile. A thin film 460 is formed on the elastic layer 450 for protection and cosmetic purposes.

In usage, an adhesive material formed on the lower surface of the stretchable and permeable substrate 405 is attached the user's skin, so that the bottom of the thermal conductive cup 302 is in tight contact with a user's skin to accurately measure temperature, electrical, or pressure signals from the user's skin, or apply electrical, thermal, or mechanical signals to the user's skin. The semiconductor chip 420 receives an electric signal from the temperature sensor 301 in response to a temperature measurement of the user's skin.

Similar to the description above, the multi-purpose wearable patch 400 can conduct dynamic measurement and dynamic treatment for applications in personalized medicine. In dynamic measurement, the sensing unit 300 and the sensor unit 450 the type(s), the timing, and frequencies of the measurement(s) by the sensing unit 300 in response to the types of treatment applied by the heater 412B under the control of the semiconductor chip 420. For example, based on the timing, the durations, intervals, and amplitudes of the treatment electric signals, the timing, the frequencies, the durations and the type(s) of the measurement(s) can be varied to more accurately and more timely monitor the user's health conditions.

Similarly, in dynamic treatment, the semiconductor chip 420 can general the treatment electric signals at durations, intervals, and amplitudes based on the measurement data obtained from the sensing units 300, 450, as described below. For example, the electrotherapy stimulation treatment can be adjusted based on the user's skin temperature, heart beats, and blood pressure measured by the sensing units 300, 450. User's bio vital signals may indicate user's stress levels, which can be treated by appropriate waveforms of electrical signals for heat or electrical treatments.

Furthermore, the semiconductor chip 420 can control the circuit to switch the sensing units 300, 450 and the heater 412B between measurement mode, a treatment mode, an off mode or a dynamic mode. The mode switching can be specified in the treatment plan received from an external device, or dynamically adjusted according to the user's vital signals and responsiveness to treatment.

Other details about wearable patches capable of performing measurement and charging functions are disclosed in commonly assigned U.S. patent application Ser. No. 15/423,585, titled "A wearable patch comprising three electrodes for measurement and charging", filed Feb. 3, 2017, commonly assigned U.S. patent application Ser. No. 15/406,380, titled "A wearable thermometer patch for correct measurement of human skin temperature", filed Jan. 13, 2017, and commonly assigned U.S. patent application Ser. No. 15/414,549, titled "A wearable thermometer patch for measuring temperature and electrical signals", filed Jan. 24, 2017. The disclosures in the above applications are incorporated herein by reference.

The disclosed dual purpose wearable patch and multi-purpose wearable patch are stretchable, compliant, durable, and comfortable to wear by users. The disclosed wearable thermometer patch includes a flexible substrate covered and protected by an elastic layer that increases the flexibility and stretchability.

Another advantage of the disclosed dual purpose wearable patch and multi-purpose wearable patch is that it can significantly increase wireless communication range by placing the antenna on the upper surface of the circuit substrate. The thickness of the substrate as well as the height of the thermally conductive cup can be selected to allow enough distance between the antenna and the user's skin to minimize interference of user's body to the wireless transmission signals.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination.

Only a few examples and implementations are described. Other implementations, variations, modifications and enhancements to the described examples and implementations may be made without deviating from the spirit of the present invention.

What is claimed is:

1. A multi-purpose wearable patch, comprising:
   a stretchable and permeable substrate;
   a first sensing unit mounted in the stretchable and permeable substrate, wherein the sensing unit includes a bottom portion adapted to be in contact with a user's skin, wherein the sensing unit comprises a temperature sensor in thermal contact with the bottom portion to conduct a first measurement of a user to produce a first measurement signal;
   a treatment unit configured to produce a first treatment field in the user's body, wherein the treatment unit includes one or more electrodes configured to be in electrical contact with the user's skin and to apply a voltage across the user's body;
   a circuit electrically connected with the treatment unit and the first sensing unit; and
   a semiconductor chip in connection with the circuit and configured to receive the first measurement signal from the first sensing unit, wherein the semiconductor chip is configured to produce a first treatment control signal to control the treatment unit to produce a first treatment field in the user's body.

2. The multi-purpose wearable patch of claim 1, wherein the treatment unit further includes a heater, wherein the semiconductor chip is configured to produce the first treatment control signal to control the heater to produce heat in the user's body.

3. The multi-purpose wearable patch of claim 1, wherein the sensing unit includes a second electrode that is configured to measure an electrical signal from the user's body in conjunction with the one or more electrodes attached to the stretchable and permeable substrate.

4. The multi-purpose wearable patch of claim 1, wherein the semiconductor chip is configured to produce a second treatment control signal to control the treatment unit to produce a second treatment field in the user's body.

5. The multi-purpose wearable patch of claim 1, wherein the semiconductor chip is configured to control the treatment unit to produce the first treatment field in the user's body in response to the first measurement signal.

6. The multi-purpose wearable patch of claim 5, wherein the semiconductor chip is configured to vary a type, timing, a frequency, or duration of the first treatment field in the user's body based on the first measurement signal.

7. The multi-purpose wearable patch of claim 1, wherein the semiconductor chip is configured to control the first sensing unit to vary a type, timing, a frequency, or duration of the first measurement of the user based on the first treatment field applied across the user's body.

8. The multi-purpose wearable patch of claim 1, wherein the semiconductor chip is configured to switch the treatment unit and the first sensing unit between a measurement mode and a treatment mode.

9. The multi-purpose wearable patch of claim 1, further comprising:
   a second sensing unit comprising a mechanical sensor configured to measure a pulse or blood pressure of the user's body.

10. The multi-purpose wearable patch of claim 1, further comprising:
    a second sensing unit to conduct a second measurement of a user to produce a second measurement signal.

11. The multi-purpose wearable patch of claim 10, wherein the semiconductor chip is configured to control the treatment unit to produce the first treatment field in the user's body in response to the first measurement signal and the second measurement signal.

12. The multi-purpose wearable patch of claim 11, wherein the semiconductor chip is configured to vary a type, a timing, a frequency, or duration of the first treatment field in the user's body based on the first measurement signal and the second measurement signal.

13. The multi-purpose wearable patch of claim 10, wherein the second sensing unit includes a mechanical sensor configured to measure a pulse or blood pressure of the user's body, or a temperature sensor configured to measure a temperature of the user's skin or body.

14. The multi-purpose wearable patch of claim 1, further comprising:
    a circuit substrate comprising the circuit and on the stretchable and permeable substrate, wherein the semiconductor chip is mounted on the circuit substrate; and
    a battery configured to supply power to the circuit and the semiconductor chip.

15. The multi-purpose wearable patch of claim 1, further comprising:
    an antenna in electric connection with the semiconductor chip, wherein the semiconductor chip is configured to produce electric signals to enable the antenna to wirelessly exchange measurement data based on the first measurement signal with an external device, wherein the semiconductor chip is configured to produce electric signals to enable the antenna to wirelessly exchange treatment data with an external device, wherein the first treatment control signal is at least in part based on the treatment data.

16. The multi-purpose wearable patch of claim 1, further comprising:
    an adhesive layer between the stretchable and permeable substrate and the circuit substrate.

17. The multi-purpose wearable patch of claim 1, further comprising:
    an elastic layer formed on the stretchable and permeable substrate, the circuit substrate, and the sensing unit.

* * * * *